United States Patent
Taryma et al.

(10) Patent No.: US 11,039,665 B2
(45) Date of Patent: Jun. 22, 2021

(54) RECEIVING FEEDBACK BASED ON PRESSURE SENSOR DATA AND MOVEMENT DATA

(71) Applicant: INTEL CORPORATION, Santa Clara, CA (US)

(72) Inventors: Joanna R. Taryma, Hillsboro, OR (US); Adrian Weber, Gdansk (PL)

(73) Assignee: Intel Corporation, Santa Clara, CA (US)

(*) Notice: Subject to any disclaimer, the term of this patent is extended or adjusted under 35 U.S.C. 154(b) by 451 days.

(21) Appl. No.: 15/754,543

(22) PCT Filed: Sep. 25, 2015

(86) PCT No.: PCT/US2015/052323
§ 371 (c)(1),
(2) Date: Feb. 22, 2018

(87) PCT Pub. No.: WO2017/052615
PCT Pub. Date: Mar. 30, 2017

(65) Prior Publication Data
US 2018/0255879 A1    Sep. 13, 2018

(51) Int. Cl.
*A61B 5/00*    (2006.01)
*A43D 1/00*    (2006.01)
(Continued)

(52) U.S. Cl.
CPC .............. *A43D 1/00* (2013.01); *A43B 3/0005* (2013.01); *A43B 7/14* (2013.01); *A43B 17/00* (2013.01);
(Continued)

(58) Field of Classification Search
CPC .......... A61B 5/11; A61B 5/112; A43B 3/0005; A43B 7/14; A43D 1/00
See application file for complete search history.

(56) References Cited

U.S. PATENT DOCUMENTS 9,149,222 B1* 10/2015 Zets ...................... A61B 5/1116
9,504,290 B2* 11/2016 Andoh ................. A43B 3/0005
(Continued)

FOREIGN PATENT DOCUMENTS

KR    20120130306 A    11/2012
KR    20140066341 A    6/2014
(Continued)

OTHER PUBLICATIONS

International Search Report and Written Opinion, Application No. PCT/US2015/052323, date of completion May 30, 2016, 13 pages.
(Continued)

*Primary Examiner* — Max F Hindenburg
(74) *Attorney, Agent, or Firm* — Schwegman Lundberg & Woessner. P.A.

(57) ABSTRACT

A method for providing pressure feedback is described herein. The method includes receiving, via a processor, pressure sensor data from a plurality of pressure sensors over a period of time. The method also includes receiving, via the processor, movement data from a plurality of sensors over the period of time. The method also further includes sending, via the processor, pressure sensor data and movement data to a data service. The method also includes receiving, via the processor, a feedback from data service.

25 Claims, 7 Drawing Sheets

(51) Int. Cl.
*G01L 5/00* (2006.01)
*A43B 3/00* (2006.01)
*A43B 7/14* (2006.01)
*A43B 17/00* (2006.01)
*A61B 5/103* (2006.01)
*A63B 6/00* (2006.01)
*A63B 24/00* (2006.01)
*A63B 69/00* (2006.01)
*A63B 71/06* (2006.01)
*G06F 30/00* (2020.01)

(52) U.S. Cl.
CPC .......... *A61B 5/0022* (2013.01); *A61B 5/1038* (2013.01); *A61B 5/486* (2013.01); *A61B 5/6807* (2013.01); *A61B 5/6892* (2013.01); *A63B 6/00* (2013.01); *A63B 24/0062* (2013.01); *A63B 69/0028* (2013.01); *A63B 71/0622* (2013.01); *G01L 5/00* (2013.01); *A43D 2200/00* (2013.01); *A43D 2200/60* (2013.01); *A61B 5/681* (2013.01); *A61B 2562/0219* (2013.01); *A61B 2562/0247* (2013.01); *A63B 2220/40* (2013.01); *A63B 2220/56* (2013.01); *A63B 2220/803* (2013.01); *A63B 2220/836* (2013.01); *A63B 2225/20* (2013.01); *G06F 30/00* (2020.01)

(56) References Cited

U.S. PATENT DOCUMENTS

| | | | | |
|---|---|---|---|---|
| 9,510,776 B2* | 12/2016 | Lee | ...................... | A61B 5/1116 |
| 9,673,864 B2* | 6/2017 | Czaja | ...................... | H04W 4/80 |
| 2004/0222892 A1* | 11/2004 | Balaban | ................ | A61B 5/1116 |
| | | | | 340/573.7 |
| 2010/0293799 A1 | 11/2010 | Lo et al. | | |
| 2011/0208444 A1* | 8/2011 | Solinsky | ............... | A61B 5/1122 |
| | | | | 702/41 |
| 2014/0018705 A1* | 1/2014 | Wang | ...................... | A61B 5/112 |
| | | | | 600/595 |
| 2014/0031725 A1* | 1/2014 | Jeon | ...................... | A61B 5/6807 |
| | | | | 600/595 |
| 2014/0156215 A1* | 6/2014 | Eastman | ................ | A61B 5/112 |
| | | | | 702/141 |
| 2014/0180595 A1* | 6/2014 | Brumback | ............. | A63B 24/00 |
| | | | | 702/19 |
| 2015/0182844 A1 | 7/2015 | Jang et al. | | |
| 2017/0055880 A1* | 3/2017 | Agrawal | ............... | A61B 5/7405 |
| 2017/0116869 A1* | 4/2017 | Pape | ...................... | A61H 1/0262 |

FOREIGN PATENT DOCUMENTS

| | | |
|---|---|---|
| KR | 20150088072 A | 7/2015 |
| WO | 2017052615 | 3/2017 |

OTHER PUBLICATIONS

"International Application Serial No. PCT US2015 052323, International Preliminary Report on Patentability dated Apr. 5, 2018", 11 pgs.

* cited by examiner

500

RECEIVING FEEDBACK BASED ON PRESSURE SENSOR DATA AND MOVEMENT DATA

CROSS REFERENCE TO RELATED APPLICATIONS

Pursuant to 35 U.S.C. § 371, this application is the United States National Stage Application of International Patent Application No. PCT/US2015/052323, filed on Sep. 25, 2015, the content of which is incorporated by reference as if set forth in its entirety herein.

TECHNICAL FIELD

Embodiments described herein generally relate to pressure sensor analysis. More specifically the embodiments relate to techniques for detecting changes in pressure sensor data in context of movement data over time.

BACKGROUND

Pressure sensor mats can be used to take static readings of pressure at various points in the mats. For example, an individual may stand on a pressure mat and have a pressure map generated based on the pressure points created. The pressure map be a static snapshot of the pressure detected by the pressure mat at a point in time.

BRIEF DESCRIPTION OF THE DRAWINGS

The same numbers are used throughout the disclosure and the figures to reference like components and features. Numbers in the 100 series refer to features originally found in FIG. 1; numbers in the 200 series refer to features originally found in FIG. 2; and so on.

DESCRIPTION OF THE EMBODIMENTS

As described above, mobile devices can be used to track the progress of a run, such as how much time is left and the average running speed, based on sensor data. However, mobile devices cannot determine whether a runner is running properly or efficiently. For example, improper running movements may result in orthopedic issues and/or poor athletic performance.

In addition, pressure on specific body parts can be measured statically in one snapshot, without consideration of the impact that motion has on actual pressure. Such sensor data is not analyzed based on speed and acceleration, or in the context of specific body motions. For example, pressure sensor maps generated by machines that detect pressure sensor data for customized shoe inserts may not use movement data in generating the customized shoe inserts.

The techniques described herein combine pressure sensor data with movement data to provide improved feedback. In some examples, a smart device can receive pressure sensor data and detect movement data. The smart device can send the pressure sensor data and the movement data to a change-detection service. For example, the change-detection service can be a cloud-based big data service. Thus, techniques described herein provide an improved pressure feedback system. Such a system enables real-time feedback based on both pressure sensor data and movement data. Moreover, the feedback can be used to prevent orthopedic problems, improve athletic performance, and design and/or manufacture improved shoes.

In the following description and claims, the term movement data refers to data from sensors and/or detected motion events from a video camera. In some examples, the movement data can include time stamp data for coordination with time series pressure sensor data. For example, a motion event can be the detected movement of any body part, including parts of limbs such as a leg, a knee, or a foot.

Figure 1:
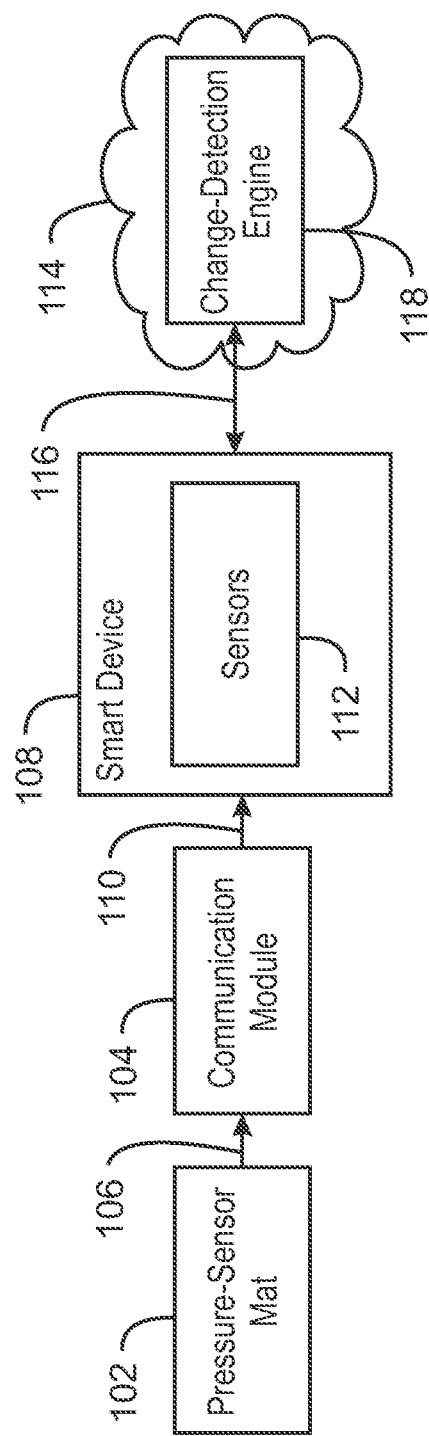
FIG. 1 is a block diagram illustrating an example system that can be used to detect changes in time series pressure data.

FIG. 1 is a block diagram illustrating an example system that can be used to detect changes in time series pressure data. In FIG. 1, the example system 100 includes a pressure-sensor 102 coupled to a communication module 104 via a link 106. The example system 100 also includes a smart device coupled to the communication module 104 via a link 110. For example, the smart device 108 can be a smart watch, a smart bracelet, a smart phone, among other possible smart devices. The smart device 108 includes movement sensors 112 and is coupled to the data service 114 via a network connection 116. The data service 114 includes a change-detection engine 118.

In the example system 100, a pressure-sensor mat 102 including one or more pressure sensors receives pressure and converts the pressure into pressure sensor data, such as one or more pressure maps. For example, the pressure-sensor mat 102 can include an elastic surface containing one or more pressures sensors that can provide pressure sensor data to a processing unit in the mat. In some examples, the pressure sensor data can include the time at which various pressures were detected and the magnitude and location of the detected pressure.

The pressure sensor mat 102 can send the pressure sensor data to the communication module 104 via link 106. The communication module 104 can include, for example, a wireless transmitter to couple to the smart device 108 via link 110. For example, link 110 can be a wireless connection, such as a short range radio connection, a wireless local area network connection, a personal area network connection, or any other suitable wireless connection.

The smart device 108 can receive the pressure sensor data from the communication module 104. The smart device 108 can also detect sensor data from one or more sensors 112 in the smart device 108. In some examples, the sensors may include an accelerometer, a speedometer, a gyroscope, or the like. For example, the sensor data can include speed and/or acceleration. The smart device 108 can include time data with the sensor data to generate movement data. For example, the movement data may be generated for the same period of time of the pressure sensor data.

Still referring to FIG. 1, the smart device 108 can send the pressure sensor data and the movement data to the data service 114. The data service 114 can forward the pressure sensor data and the movement data to the change-detection engine 118. For example, the pressure sensor data and movement data can be sent to the change detection engine 118 via a link 116. For example, the link 116 can be a wireless location area network connection, a cellular data connection, a general packet radio service (GPRS), or any suitable wireless connection. The change detection engine 118 can receive the pressure sensor data and the movement data via a network connection 116 and perform analysis on the data. In some examples, the change detection engine 118 can generate a model based on the pressure sensor data and the movement data. The data service 114 can store the received data as time series rows, with pressure measurements and detected movement combined. In some examples, the model can be used for comparison with future collected data as discussed below. The change detection service 118 can then detect a change. For example, the change can be detected based on standard deviation from the past observations as embodied in the model.

In some examples, the pressure sensor data may be from one or more pressure mats inside a pair of shoes. For example, each shoe can include a pressure mat in the shape of the sole. In some examples, separate pressure mats may be used for the heel and the toes of each shoe. The pressure sensor data can be used with the movement data to detect a change in the way a person runs in the shoes. For example, the time series data can be used to detect a change that may correlate with a change in running movements. In some examples, the data service 114 can return feedback to the smart device 108. For example, the feedback may be a real-time indication that a runner may be running improperly. The runner can be alerted by the smart device 108 and correct running movements accordingly. Thus, the smart device 108 can improve the running habits of people as they are performing. For example, improved running habits may result in reduced injuries and improved running performance. Moreover, the techniques can improve the usability and/or scope of functions of smart devices 108 by enabling the devices to provide real-time feedback based on both pressure sensor data and movement data.

In some examples, the change-detection engine 118 can aggregate and analyze data from a plurality of devices. For example, the change-detection engine 118 can receive pressure sensor data and movement data from a plurality of smart devices 108 via the data service 114. The change-detection engine 118 can then aggregate and analyze the pressure-sensor data and movement data from the plurality of smart devices 108. In some examples, the change-detection service 118 can use the aggregated data from other devices in order to detect a difference in the time series data. For example, the time series data generated from the pressure sensor data and the movement data can be compared to and/or matched with data from thousands or more other devices.

The diagram of FIG. 1 is not intended to indicate that the example system 100 is to include all of the components shown in FIG. 1. Rather, the example system 100 can include fewer or additional components not illustrated in FIG. 1 (e.g., additional pressure-sensor mats, communication modules, sensors, smart devices, services, engines, etc.).

Figure 2:
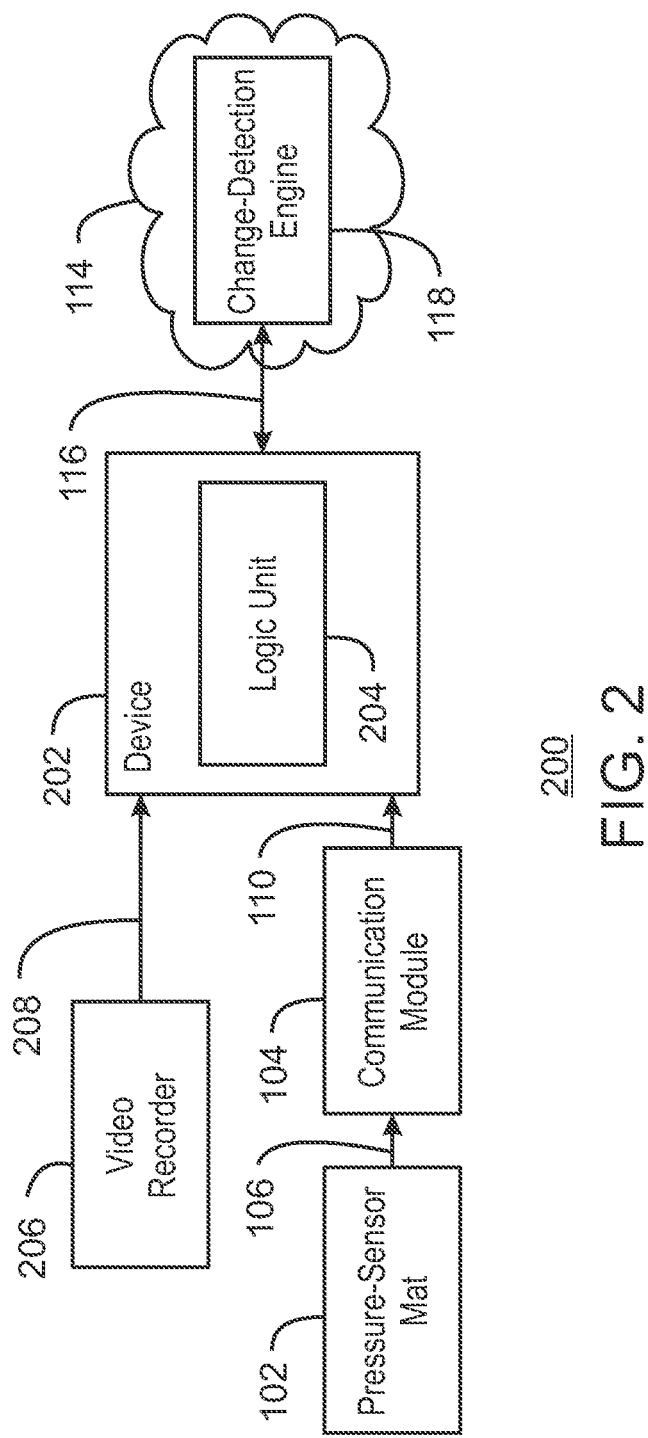
FIG. 2 is a block diagram of another example system that can be used to detect changes in time series pressure data.

FIG. 2 is a block diagram of an example system providing for a context-aware naming service according to the techniques described herein. In FIG. 2, the example system 200 includes a pressure sensor mat 102 coupled to a communication module via a link 106. The communication module is further coupled to a device 202 via a link 110. For example, the device 202 can be any suitable computing device. The device 202 includes a logic unit 204 for detecting motion events. The device 202 is also coupled to a video recorder 206 via a link 208. The device 202 is further coupled to a data service 114 via a link 116. The data service 114 can include a change-detection engine 118.

In the example system of FIG. 2, the device 202 can receive pressure sensor data captured by one or more pressure sensors inside the pressure-sensor mat 102 via the communication module 104. The communication module 104 can include, for example, a wireless transmitter and the link 110 can be a wireless link such as a wireless local area network connection or short range radio connection.

In addition, the device 202 can also receive recorded video from the video recorder 206. For example, the video recorder 206 can include a video camera and can be compatible with the logic unit 204. For example, the logic unit 204 can receive video from the video recorder and detect one or more motion events. A motion event can include, for example, the movement of an arm, a leg, a hand, as well as a facial expression. The detected motion event can be sent to the data service 104 along with pressure sensor data. In some examples, additional movement data from sensor in the device 202 may also be sent to the data service 104. The data service 104 can forward the pressure sensor data and movement data to the change-detection engine 118.

Still referring to FIG. 2, the change-detection engine 108 can analyze the movement data and the pressure sensor data. For example, the change-detection engine 108 can analyze changes in the pressure sensor data in context of motion events, speed, acceleration, and positions from a gyroscope, among other movement data. The data service 104 can then provide feedback based on results of the analysis as discussed in different examples with respect to FIGS. 3-5 below.

The diagram of FIG. 2 is not intended to indicate that the example system 200 is to include all of the components shown in FIG. 2. Rather, the example system 200 can include fewer or additional components not illustrated in FIG. 2 (e.g., additional pressure-sensor mats, communication modules, video recorders, devices, logic units, services, engines, etc.).

Figure 3:
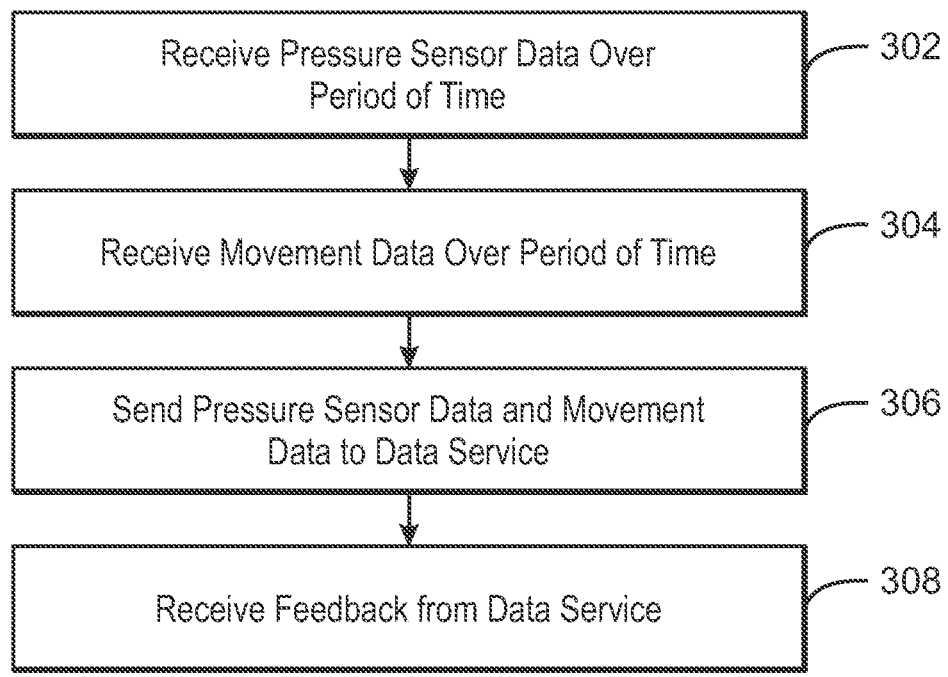
FIG. 3 is a process flow diagram illustrating an example method that depicts change detection based on pressure sensor data and movement data.

FIG. 3 is a process flow diagram illustrating an example method that depicts change detection based on pressure sensor data and movement data. The example method of FIG. 3 is generally referred to by the reference number 300 and can be implemented using the example mobile computing device 600 of FIG. 6.

At block 302, the mobile computing device receives pressure sensor data over a period of time. In some examples, the pressure-sensor data can include data from a pressure-sensor mat in the form of one or more pressure maps. For example, the pressure-sensor data can include data from a wearable pressure-sensor mat.

At block 304, the mobile computing device receives movement data over the period of time. For example, the movement data can include accelerometer data, speedometer data, and gyroscope data, among other sensory data. In some examples, the movement data can include one or more motion events detected by a logic unit coupled to a video camera.

At block 306, the mobile computing device sends the pressure sensor data and movement data to a data service. For example, the data service can be a cloud-implemented data service. In some examples, the data service can include a big data change-detection engine, including a database having information from a plurality of mobile computing devices.

At block 308, the mobile computing device receives feedback from the data service. For example, the feedback can be a change detected based on standard deviation from past pressure-sensor data and/or movement data of the mobile computing device. In some examples, the change can be detected based on a standard deviation from pressure-sensor data and/or movement data distribution of values from a plurality of mobile computing devices. For example, the feedback can include a current state of a target object based on standard deviation from previous pressure sensor data and movement data. In some examples, the feedback can be an alert sent to the mobile computing device when the standard deviation exceeds a period of threshold value. In one example, a mobile computing device can dynamically display an alert. For example, the alert can inform a user that the user has changed a normal pattern of behavior with respect to walking, running, or any other activity. In some examples, the change in behavior may lead to health problems. The user may thus alter their behavior accordingly.

In some examples, the feedback can include a customized design structure. For example, the customized design structure can be based on the pressure sensor data and the movement data. In some examples, the customized design structure can be a customized shoe. The shoe may be designed to provide increased support for pressures generated during a plurality of movements.

In some examples, the feedback can include a detected orthopedic deformity. For example, the detected orthopedic deformity can include flat feet among other orthopedic deformities. In some examples, the deformity may be detected via a comparison with a model structure. For example, the model structure may be pre-configured and/or generated from information from a plurality of mobile computing devices. In some examples, the feedback can include a detected impairment. For example, the impairment can include any injury resulting in a detectable change in pressure. For example, the change may be detected via a comparison with a model structure. In some examples, the model structure can be pre-configured, based on past pressure sensor data and movement data from the device, or based on pressure sensor data and movement data from a plurality of devices.

This process flow diagram is not intended to indicate that the blocks of the method 300 are to be executed in any particular order, or that all of the blocks are to be included in every case. Further, any number of additional blocks not shown may be included within the method 300, depending on the details of the specific implementation.

Figure 4:
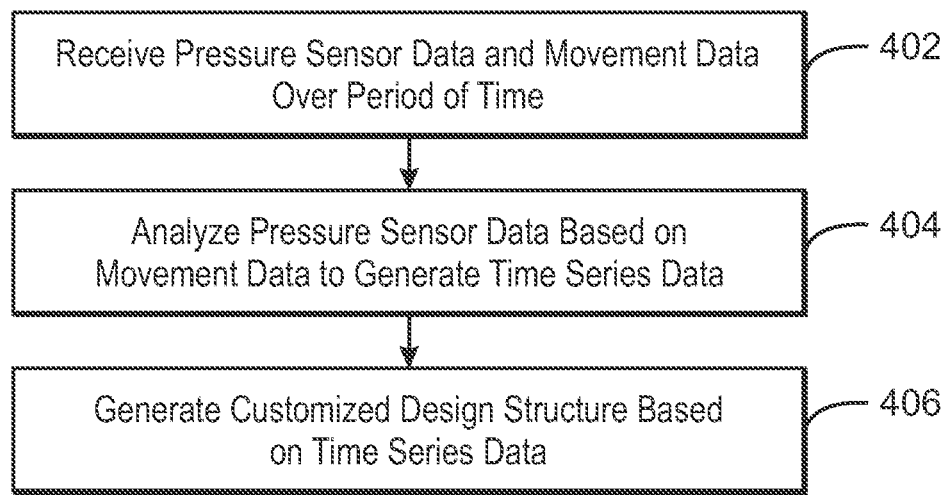
FIG. 4 is a process flow diagram illustrating an example method that depicts generating customized design structures based on pressure sensor data and movement data.

FIG. 4 is a process flow diagram illustrating an example method that depicts generating customized design structures based on pressure sensor data and movement data. The example method of FIG. 4 is generally referred to by the reference number 400 and can be implemented using the change-detection engine of FIGS. 1 and 2 above.

At block 402, the change-detection engine receives pressure sensor data and movement data over a period of time. For example, the movement data can include a motion event detected by a depth sensor corresponding to a limb movement or a body movement. The pressure data can include data from a wearable pressure-sensor mat. For example, the wearable pressure-sensor mat can be inside a shoe. In one example, a video camera may have recorded a person running with the wearable pressure-sensor shoe and detect motion events over a period of amount of time.

At block 404, the change-detection engine analyzes the pressure sensor data based on the movement data to generate time series data. For example, time series data can be generated by analyzing the pressure-sensor data and the movement data over time.

At block 406, the change-detection engine generates a customized design structure based on the time series data. For example, based on how pressure of particular parts of a shoe changes when walking or running, a customized shoe design can be generated to provide pressure support for particular activities and/or the particular person providing the pressure-sensor data and movement data. In some examples, the service can generate a design structure with balanced pressure support based on time series data. For example, a shoe design can be generated to provide pressure support that provides support during walking as well as running. In some examples, the service can compare the time series data with preexisting time series data to detect a corresponding preexisting design structure that correlates with the time series data. For example, existing shoe designs may be similar to the customized design structure generated by the service. The service can return existing shoe designs providing suitable support for the particular individual. In some examples, the service can return existing shoe designs for particular activities. For example, activities such as running, lifting weights, playing sports, etc., may result in customized shoe designs providing pressure support for each activity based on the pressure-sensor data and the movement data.

This process flow diagram is not intended to indicate that the blocks of the method 400 are to be executed in any particular order, or that all of the blocks are to be included in every case. Further, any number of additional blocks not shown may be included within the method 400, depending on the details of the specific implementation.

Figure 5:
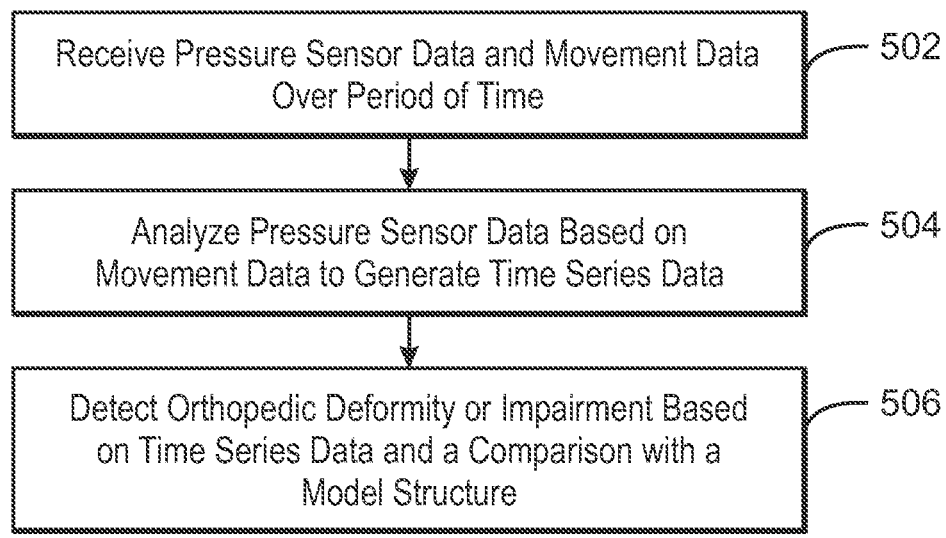
FIG. 5 is a process flow diagram illustrating an example method that depicts detecting an orthopedic deformity or impairment based on time series data.

FIG. 5 is a process flow diagram illustrating an example method that depicts detecting an orthopedic deformity or impairment based on time series data. The example method of FIG. 5 is generally referred to by the reference number 500 and can be implemented using the change-detection engine of FIGS. 1 and 2 above.

At block 502, the change-detection engine receives pressure sensor data and movement data over a period of time. For example, the movement data can include a motion event detected by a depth sensor corresponding to a limb movement or a body movement. The pressure data can include data from a wearable pressure-sensor mat. For example, the wearable pressure-sensor mat can be inside a shoe. In one example, a video camera may have recorded a person running with the wearable pressure-sensor shoe and detect motion events over a period of amount of time.

At block 504, the change-detection engine analyzes the pressure sensor data based on the movement data to generate time series data. For example, the time series data can be generated by analyzing the pressure-sensor data and the movement data over time.

At block 506, the change-detection engine detects an orthopedic deformity or impairment based on the time series data and a comparison with a model structure. For example, the orthopedic deformity can be flat feet or any other orthopedic deformity. In some examples, the model structure can be predefined for the engine or learned by the engine via analysis of past observations. For example, the model structure can be a predefined pattern of pressure indicating normal foot pressure. In some examples, the change-detection engine can provide the detected deformity to the data service 104. The data service 104 can provide feedback including the detected deformity to a computing device. In some examples, the computing device can include a smart device.

This process flow diagram is not intended to indicate that the blocks of the method 500 are to be executed in any particular order, or that all of the blocks are to be included in every case. Further, any number of additional blocks not shown may be included within the method 500, depending on the details of the specific implementation.

Figure 6:
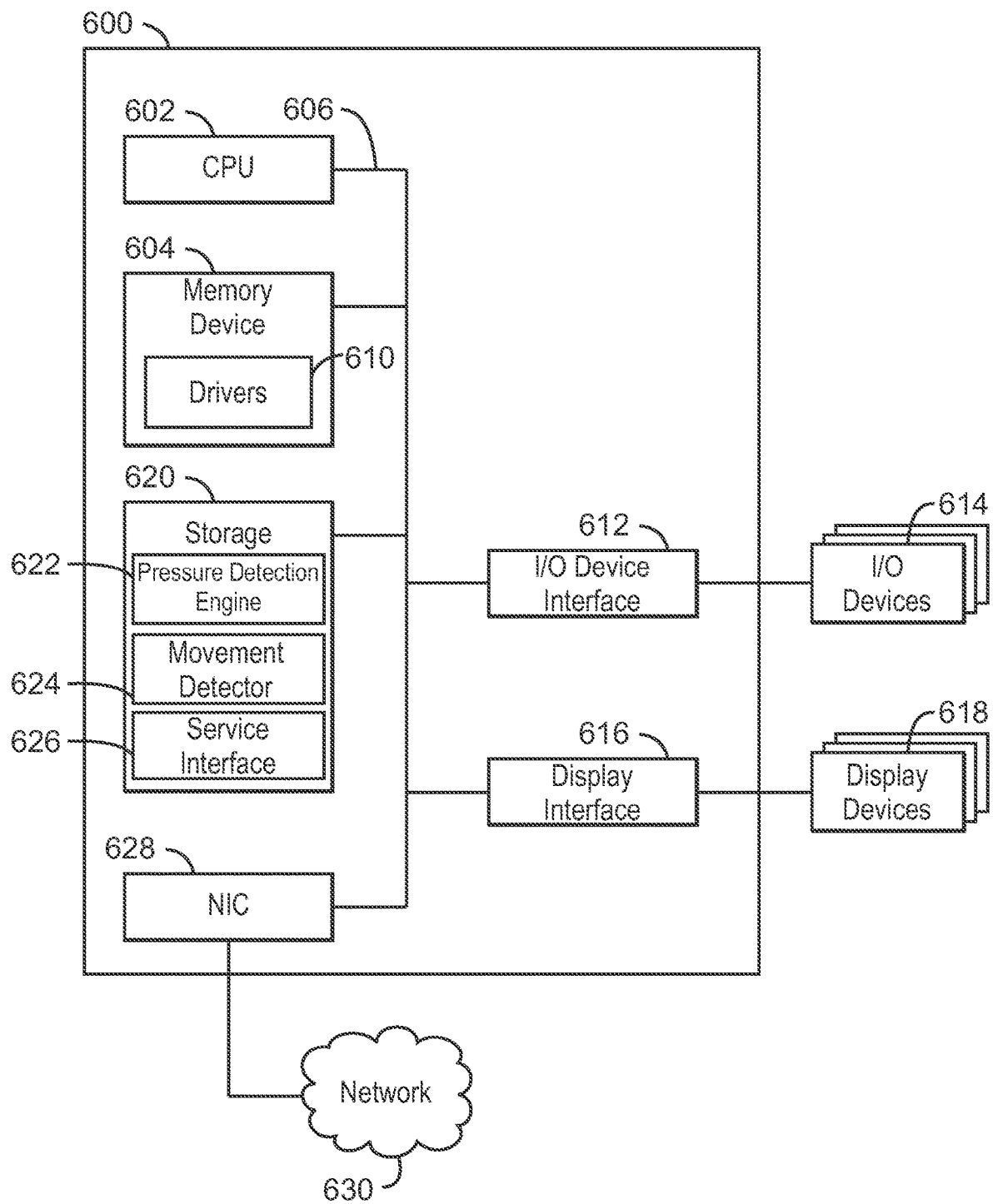
FIG. 6 is a block diagram illustrating an example computing device that can be used as a node for a change detection service.

FIG. 6 is a block diagram illustrating an example computing device that can be used as a node for a change detection service. The computing device 600 may be, for example, a laptop computer, desktop computer, tablet computer, mobile device, or server, among others. The computing device 600 may include a central processing unit (CPU) 602 that is configured to execute stored instructions, as well as a memory device 604 that stores instructions that are executable by the CPU 602. The CPU 602 may be coupled to the memory device 604 by a bus 606. Additionally, the CPU 602 can be a single core processor, a multi-core processor, a computing cluster, or any number of other configurations. Furthermore, the computing device 600 may include more than one CPU 602. The memory device 604 can include random access memory (RAM), read only memory (ROM), flash memory, or any other suitable memory systems. For example, the memory device 604 may include dynamic random access memory (DRAM).

The memory device 604 can include random access memory (RAM), read only memory (ROM), flash memory, or any other suitable memory systems. For example, the memory device 604 may include dynamic random access memory (DRAM). The memory device 604 may include device drivers 610 that are configured to execute the instructions for device discovery. The device drivers 610 may be software, an application program, application code, or the like.

The CPU 602 may also be connected through the bus 606 to an input/output (I/O) device interface 612 configured to connect the computing device 600 to one or more I/O devices 614. The I/O devices 614 may include, for example, a keyboard and a pointing device, wherein the pointing device may include a touchpad or a touchscreen, among others. The I/O devices 614 may be built-in components of the computing device 600, or may be devices that are externally connected to the computing device 600. In some examples, the memory 604 may be communicatively coupled to I/O devices 614 through direct memory access (DMA).

The CPU 602 may also be linked through the bus 606 to a display interface 616 configured to connect the computing device 600 to a display device 618. The display device 618 may include a display screen that is a built-in component of the computing device 600. The display device 618 may also include a computer monitor, television, or projector, among others, that is internal to or externally connected to the computing device 600.

The computing device also includes a storage device 620. The storage device 620 is a physical memory such as a hard drive, an optical drive, a thumbdrive, an array of drives, or any combinations thereof. The storage device 620 may also include remote storage drives. The storage device 620 includes a pressure detection engine 622, a movement detector 624, and service interface 626. The pressure detection engine 622 can receive pressure sensor data over a period of time. For example, the pressure sensor data can include data from a pressure-sensor mat in the form of one or more pressure maps. In some examples, the pressure sensor data can include data from a wearable pressure-sensor mat. The movement detector 624 can receive movement data over the period of time. For example, the movement data can include accelerometer data, speedometer data, and gyroscope data, among other sensor data. In some examples, the movement data can include one or more motion events. The service interface 626 can send the pressure sensor data and the movement data to a data service. For example, the data service can be a distributed service hosted on one or more servers. The service interface 626 can also receive a detected change or a feedback from the data service. For example, the change can be detected based on a standard deviation from some normal distribution. For example, the normal distribution can be determined from previously collected data.

In some examples, the naming inference engine can configure an accessibility level for the device, a group of devices including the device, a service associated with the device, or any combination thereof. In some examples, the accessibility level can be associated with a gateway, group of devices associated with the gateway, a service associated with the gateway, or any combination thereof.

The computing device 600 may also include a network interface controller (NIC) 628. The NIC 628 may be configured to connect the computing device 600 through the bus 606 to a network 630. The network 630 may be a wide area network (WAN), local area network (LAN), or the Internet, among others. In some examples, the device may communicate with other devices through a wireless technology. For example, Bluetooth® or similar technology may be used to connect with other devices.

The block diagram of FIG. 6 is not intended to indicate that the computing device 600 is to include all of the components shown in FIG. 6. Rather, the computing system 600 can include fewer or additional components not illustrated in FIG. 6, such as additional engines, additional network interfaces, and the like. The computing device 600 may include any number of additional components not shown in FIG. 6, depending on the details of the specific implementation. Furthermore, any of the functionalities of the CPU 602 may be partially, or entirely, implemented in hardware and/or in a processor. For example, the functionality of the pressure detection engine 622, the movement detector 624, and the service interface 626 may be implemented with an application specific integrated circuit, in logic implemented in a processor, in logic implemented in a specialized graphics processing unit, or in any other device.

Figure 7:
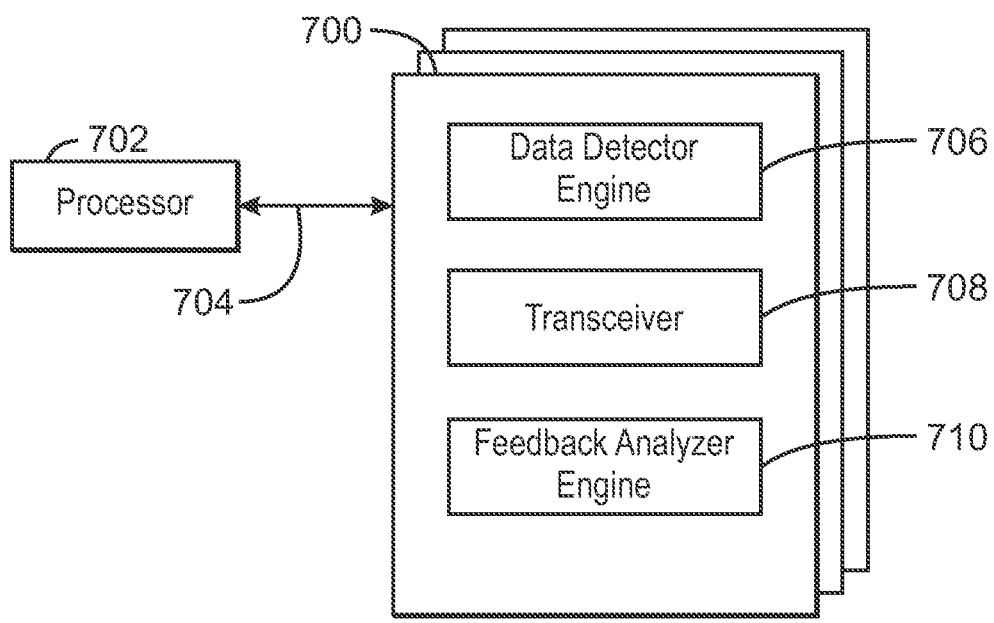
FIG. 7 is a block diagram showing computer readable media that store code for detecting changes based on time series data.

FIG. 7 is a block diagram showing computer readable media 700 that store code for naming of devices. The computer readable media 700 may be accessed by a processor 702 over a computer bus 704. Furthermore, the computer readable medium 700 may include code configured to direct the processor 702 to perform the methods described herein. In some embodiments, the computer readable media 700 may be non-transitory computer readable media. In some examples, the computer readable media 700 may be storage media. However, in any case, the computer readable media do not include transitory media such as signals, and the like.

The block diagram of FIG. 7 is not intended to indicate that the computer readable media 700 is to include all of the components shown in FIG. 7. Further, the computer readable media 700 may include any number of additional components not shown in FIG. 7, depending on the details of the specific implementation.

The various software components discussed herein may be stored on one or more computer readable media 700, as indicated in FIG. 7. For example, a data detector engine 706 may be configured to receive pressure sensor data over a period of time. For example, the pressure sensor data can include data from a pressure-sensor mat in the form of one or more pressure maps. In some examples, the pressure sensor data can include data from a wearable pressure-sensor mat. The data detector engine 706 may also be configured to receive movement data over the period of time. For example, the movement data can include accelerometer data, speedometer data, and gyroscope data, among other sensor data. In some examples, the movement data can include one or more motion events. The transceiver 708 may be configured to send the pressure sensor data and the movement data to a data service. For example, the data service can be a distributed service hosted on one or more servers. The transceiver 708 can also be configured to receive a detected change or a feedback from the data service. For example, the change can be detected based on a standard deviation from some normal distribution. For example, the distribution can be previously collected data. In some examples, the previously collected data may have been used to generate a model to be used for comparison.

In some examples, the feedback analyzer engine 710 can detect an orthopedic deformity or impairment based on the feedback. In some examples, the feedback analyzer engine 710 can detect an orthopedic deviation based on a detected change. In some examples, the feedback analyzer engine 710 can generate a customized shoe design structure with balanced pressure support based on the feedback. For example, the feedback analyzer 710 can receive results of a comparison of pressure-mat metrics and model structure. The results can include data indicating neuralgic points that are either overloaded or underloaded. In some examples, a shoe design can be generated based on the overloaded or underloaded neuralgic points. In some examples, the feedback analyzer engine 710 can dynamically display an alert based on the detected change.

The block diagram of FIG. 7 is not intended to indicate that the computer readable media 700 is to include all of the components shown in FIG. 7. Further, the computer readable media 700 may include any number of additional components not shown in FIG. 7, depending on the details of the specific implementation.

EXAMPLES

The following examples pertain to further embodiments.

Example 1 is a system for sensing pressure. The system includes a pressure detection engine to receive pressure sensor data captured over a period of time; a movement detector to receive movement data captured over the period of time; and a service interface to send the pressure sensor data and the movement data to a data service and receive a feedback from the data service.

Example 2 includes the system of example 1, including or excluding optional features. In this example, the movement data includes accelerometer data, speedometer data, gyroscope data, or any combination thereof.

Example 3 includes the system of any one of examples 1 to 2, including or excluding optional features. In this example, the movement data includes a motion event detected by a depth sensor corresponding to a limb movement or a body movement.

Example 4 includes the system of any one of examples 1 to 3, including or excluding optional features. In this example, the pressure sensor data includes a pressure map from a pressure-sensor mat.

Example 5 includes the system of any one of examples 1 to 4, including or excluding optional features. In this example, the pressure sensor data includes data from a wearable pressure-sensor mat.

Example 6 includes the system of any one of examples 1 to 5, including or excluding optional features. In this example, the feedback includes a customized design structure based on the pressure sensor data and the movement data. Optionally, the customized design structure can be a customized shoe. Optionally, the feedback includes a detected preexisting design structure that correlates with the pressure sensor data and the movement data.

Example 7 includes the system of any one of examples 1 to 6, including or excluding optional features. In this example, the feedback includes a detected orthopedic deformity.

Example 8 includes the system of any one of examples 1 to 7, including or excluding optional features. In this example, the feedback includes a detected impairment.

Example 9 is a method for providing pressure feedback. The method includes receiving, via a processor, pressure sensor data from a plurality of pressure sensors over a period of time. The method also includes receiving, via the processor, movement data from a plurality of sensors over the period of time. The method further includes sending, via the processor, pressure sensor data and movement data to a data service. The method also further includes receiving, via the processor, a feedback from the data service.

Example 10 includes the method of example 9, including or excluding optional features. In this example, the feedback includes a detected change based on standard deviation from previous data from the plurality of pressure sensors.

Example 11 includes the method of any one of examples 9 to 10, including or excluding optional features. In this example, the feedback includes a current state of a target object based on standard deviation from previous pressure sensor data and movement data.

Example 12 includes the method of any one of examples 9 to 11, including or excluding optional features. In this example, the method includes generating a customized shoe design structure with balanced pressure support based on the feedback.

Example 13 includes the method of any one of examples 9 to 12, including or excluding optional features. In this example, the method includes detecting an orthopedic abnormality by comparing the feedback to feedback for a plurality of other devices.

Example 14 includes the method of any one of examples 9 to 13, including or excluding optional features. In this example, the method includes detecting an orthopedic deviation based on the feedback.

Example 15 includes the method of any one of examples 9 to 14, including or excluding optional features. In this example, the method includes manufacturing a shoe with orthopedic support based on a shoe design structure generated based on the feedback.

Example 16 includes the method of any one of examples 9 to 15, including or excluding optional features. In this example, the method includes manufacturing a shoe insert for orthopedic support based on a shoe design structure generated from the feedback.

Example 17 includes the method of any one of examples 9 to 16, including or excluding optional features. In this example, the method includes dynamically displaying an alert based on the feedback.

Example 18 includes the method of any one of examples 9 to 17, including or excluding optional features. In this example, the method includes detecting an orthopedic deformity or impairment based on the feedback.

Example 19 is a tangible, non-transitory, computer-readable medium comprising instructions that, when executed by a processor, direct the processor to detect pressure changes. The computer-readable medium includes instructions that direct the processor to receive pressure sensor data over a period of time; receive movement data over the period of time; send the pressure sensor data and the movement data to a data service; and receive a feedback from the data service.

Example 20 includes the computer-readable medium of example 19, including or excluding optional features. In this example, the movement data includes accelerometer data, speedometer data, gyroscope data, or any combination thereof.

Example 21 includes the computer-readable medium of any one of examples 19 to 20, including or excluding optional features. In this example, the movement data includes a motion event detected by a depth sensor corresponding to a limb movement or a body movement.

Example 22 includes the computer-readable medium of any one of examples 19 to 21, including or excluding optional features. In this example, the pressure sensor data includes a pressure map from a pressure-sensor mat.

Example 23 includes the computer-readable medium of any one of examples 19 to 22, including or excluding optional features. In this example, the pressure sensor data includes data from a wearable pressure-sensor mat.

Example 24 includes the computer-readable medium of any one of examples 19 to 23, including or excluding optional features. In this example, the computer-readable medium includes instructions to receive results of a comparison of pressure-mat metrics and a model structure, wherein the results include data indicating neuralgic points that are overloaded or underloaded.

Example 25 includes the computer-readable medium of any one of examples 19 to 24, including or excluding optional features. In this example, the computer-readable medium includes instructions to detect an orthopedic deformity or impairment based on the feedback.

Example 26 includes the computer-readable medium of any one of examples 19 to 25, including or excluding optional features. In this example, the computer-readable medium includes instructions to detect an orthopedic deviation based on the feedback.

Example 27 includes the computer-readable medium of any one of examples 19 to 26, including or excluding optional features. In this example, the computer-readable medium includes instructions to generate a customized shoe design structure with balanced pressure support based on the feedback.

Example 28 includes the computer-readable medium of any one of examples 19 to 27, including or excluding optional features. In this example, the computer-readable medium includes instructions to dynamically display an alert based on the feedback.

Example 29 is an apparatus for sensing pressure. The apparatus includes instructions that direct the processor to a pressure detection engine to receive pressure sensor data captured over a period of time; a movement detector to receive movement data captured over the period of time; and a service interface to send the pressure sensor data and the movement data to a data service and receive a feedback from the data service.

Example 30 includes the apparatus of example 29, including or excluding optional features. In this example, the movement data includes accelerometer data, speedometer data, gyroscope data, or any combination thereof.

Example 31 includes the apparatus of any one of examples 29 to 30, including or excluding optional features. In this example, the movement data includes a motion event detected by a depth sensor corresponding to a limb movement or a body movement.

Example 32 includes the apparatus of any one of examples 29 to 31, including or excluding optional features. In this example, the pressure sensor data includes a pressure map from a pressure-sensor mat.

Example 33 includes the apparatus of any one of examples 29 to 32, including or excluding optional features. In this example, the pressure sensor data includes data from a wearable pressure-sensor mat.

Example 34 includes the apparatus of any one of examples 29 to 33, including or excluding optional features. In this example, the feedback includes a customized design structure based on the pressure sensor data and the movement data. Optionally, the customized design structure can be a customized shoe. Optionally, the feedback includes a detected preexisting design structure that correlates with the pressure sensor data and the movement data.

Example 35 includes the apparatus of any one of examples 29 to 34, including or excluding optional features. In this example, the feedback includes a detected orthopedic deformity.

Example 36 includes the apparatus of any one of examples 29 to 35, including or excluding optional features. In this example, the feedback includes a detected impairment.

Example 37 is a system for sensing pressure. The system includes instructions that direct the processor to means for receiving pressure sensor data captured over a period of time; means for receiving movement data captured over the period of time; and means for sending the pressure sensor data and the movement data to a data service and receive a feedback from the data service.

Example 38 includes the system of example 37, including or excluding optional features. In this example, the movement data includes accelerometer data, speedometer data, gyroscope data, or any combination thereof.

Example 39 includes the system of any one of examples 37 to 38, including or excluding optional features. In this example, the movement data includes a motion event detected by a depth sensor corresponding to a limb movement or a body movement.

Example 40 includes the system of any one of examples 37 to 39, including or excluding optional features. In this example, the pressure sensor data includes a pressure map from a pressure-sensor mat.

Example 41 includes the system of any one of examples 37 to 40, including or excluding optional features. In this example, the pressure sensor data includes data from a wearable pressure-sensor mat.

Example 42 includes the system of any one of examples 37 to 41, including or excluding optional features. In this example, the feedback includes a customized design structure based on the pressure sensor data and the movement data. Optionally, the customized design structure can be a customized shoe. Optionally, the feedback includes a detected preexisting design structure that correlates with the pressure sensor data and the movement data.

Example 43 includes the system of any one of examples 37 to 42, including or excluding optional features. In this example, the feedback includes a detected orthopedic deformity.

Example 44 includes the system of any one of examples 37 to 43, including or excluding optional features. In this example, the feedback includes a detected impairment.

Some embodiments may be implemented in one or a combination of hardware, firmware, and software. Some embodiments may also be implemented as instructions stored on a computer readable medium, which may be read and executed by a computing platform to perform the operations described herein. A computer readable medium may include any mechanism for storing or transmitting information in a form readable by a machine, e.g., a computer. For example, a computer readable medium may include read only memory (ROM); random access memory (RAM); magnetic disk storage media; optical storage media; flash memory devices; or the interfaces that transmit and/or receive signals, among others.

An embodiment is an implementation or example. Reference in the specification to "an embodiment", "one embodiment", "some embodiments", "various embodiments", or "other embodiments" means that a particular feature, structure, or characteristic described in connection with the embodiments is included in at least some embodiments, but not necessarily all embodiments, of the inventions. The various appearances of "an embodiment", "one embodiment" or "some embodiments" are not necessarily all referring to the same embodiments. Elements or aspects from an embodiment can be combined with elements or aspects of another embodiment.

Not all components, features, structures, characteristics, etc. described and illustrated herein need be included in a particular embodiment or embodiments. If the specification states a component, feature, structure, or characteristic "may", "might", "can" or "could" be included, for example, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

It is to be noted that, although some embodiments have been described in reference to particular implementations, other implementations are possible according to some embodiments. Additionally, the arrangement and/or order of circuit elements or other features illustrated in the drawings and/or described herein need not be arranged in the particular way illustrated and described. Many other arrangements are possible according to some embodiments.

In each system shown in a figure, the elements in some cases may each have a same reference number or a different reference number to suggest that the elements represented could be different and/or similar. However, an element may be flexible enough to have different implementations and work with some or all of the systems shown or described herein. The various elements shown in the figures may be the same or different. Which one is referred to as a first element and which is called a second element is arbitrary.

The inventions are not restricted to the particular details listed herein. Indeed, those skilled in the art having the benefit of this disclosure will appreciate that many other variations from the foregoing description and drawings may be made within the scope of the present inventions. Accordingly, it is the following claims including any amendments thereto that define the scope of the inventions.

What is claimed is:

1. A system for sensing pressure, comprising:
    a pressure detection engine implemented at least in part in a circuit, to receive pressure sensor data captured over a period of time;
    a movement detector implemented at least in part in a circuit, to receive movement data captured over the period of time, the movement data captured using a camera; and
    a service interface implemented at least in part in a circuit, to send the pressure sensor data and movement data to a data service and receive a feedback from the data service.

2. The system of claim 1, wherein the movement data comprises accelerometer data, speedometer data, gyroscope data, or any combination thereof.

3. The system of claim 1, wherein the movement data comprises a motion event.

4. The system of claim 1, wherein the pressure sensor data comprises a pressure map from a pressure-sensor mat.

5. The system of claim 1, wherein the pressure sensor data comprises data from a wearable pressure-sensor mat.

6. The system of claim 1, wherein the feedback comprises a customized design structure based on the pressure sensor data and the movement data.

7. The system of claim 6, wherein the customized design structure comprises a customized shoe.

8. The system of claim 6, wherein the feedback comprises a detected preexisting design structure that correlates with the pressure sensor data and the movement data.

9. The system of claim 1, wherein the feedback comprises a detected orthopedic deformity.

10. The system of claim 1, wherein the feedback comprises a detected impairment.

11. A method for providing pressure feedback, comprising:
    receiving, via a processor, pressure sensor data from a plurality of pressure sensors over a period of time;
    receiving, via the processor, movement data from a plurality of sensors over the period of time, the movement data captured using a camera;
    sending, via the processor, pressure sensor data and movement data to a data service; and
    receiving, via the processor, a feedback from the data service.

12. The method of claim 11, wherein the feedback comprises a detected change based on standard deviation from previous data from the plurality of pressure sensors.

13. The method of claim 11, further comprising generating a customized shoe design structure with balanced pressure support based on the feedback.

14. The method of claim 11, further comprising detecting an orthopedic abnormality by comparing the feedback to feedback for a plurality of other devices.

15. A tangible, non-transitory, computer-readable medium comprising instructions that, when executed by a processor, direct the processor to detect pressure changes, the instructions to direct the processor to:

receive pressure sensor data over a period of time;
receive movement data over the period of time, the movement data captured using a camera;
send the pressure sensor data and the movement data to a data service; and
receive a feedback from the data service.

16. The tangible, non-transitory, computer-readable medium of claim 15, comprising instructions to detect an orthopedic deformity or impairment based on the feedback.

17. The tangible, non-transitory, computer-readable medium of claim 15, comprising instructions to detect an orthopedic deviation based on the feedback.

18. The tangible, non-transitory, computer-readable medium of claim 15, comprising instructions to generate a customized shoe design structure with balanced pressure support based on the feedback.

19. The tangible, non-transitory, computer-readable medium of claim 15, comprising instructions to dynamically display an alert, based on the feedback.

20. The method of claim 11, further comprising detecting an orthopedic deviation based on the feedback.

21. The method of claim 11, further comprising manufacturing a shoe with orthopedic support based on a shoe design structure generated based on the feedback.

22. The method of claim 11, further comprising manufacturing a shoe insert for orthopedic support based on a shoe design structure generated from the feedback.

23. The method of claim 11, further comprising dynamically displaying an alert based on the feedback.

24. The method of claim 11, further comprising detecting an orthopedic deformity or impairment based on the feedback.

25. The system of claim 1, wherein the movement data includes a facial expression.

* * * * *